United States Patent [19]

Bansal et al.

[11] Patent Number: 5,451,681
[45] Date of Patent: Sep. 19, 1995

[54] PROCESS FOR PREPARING NEMATICIDAL BENZOXAZOLE AND BENZTHIAZOLE COMPOUNDS

[75] Inventors: Harjinder S. Bansal, Bracknell; Peter J. V. Cleare, Ascot, both of United Kingdom

[73] Assignee: Zeneca Limited, London, England

[21] Appl. No.: 366,068

[22] Filed: Dec. 29, 1994

[30] Foreign Application Priority Data

Jan. 13, 1994 [GB] United Kingdom ............... 9400523

[51] Int. Cl.$^6$ .................. C07D 277/74; C07D 263/58
[52] U.S. Cl. .................................... 548/173; 548/221
[58] Field of Search .................. 548/173, 165, 221; 514/367, 375

[56] References Cited

U.S. PATENT DOCUMENTS 4,724,072  2/1988  Bornengo et al. ............... 209/167

FOREIGN PATENT DOCUMENTS 0196592  10/1986  European Pat. Off. .
58-225072  12/1983  Japan .
2270689  3/1994  United Kingdom .
1648948A  5/1991  U.S.S.R. .

Primary Examiner—Robert W. Ramsuer
Assistant Examiner—Laura Cross
Attorney, Agent, or Firm—Marian T. Thomson

[57] ABSTRACT

A process for preparing a compound of formula (I)

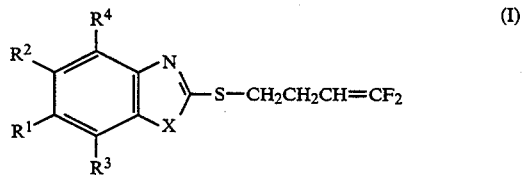

wherein X is oxygen or sulphur, by (a) reacting a substituted ortho-nitro or -nitroso phenol or a substituted ortho-nitro or -nitroso thiophenol with an alkali metal dithionite reducing agent in an alkaline reaction medium in the presence of carbon disulphide, to form a substituted 2-mercaptobenz-oxazole or -thiazole, acidifying the reaction mixture and collecting the 2-mercaptobenz-oxazole or -thiazole; and then (b) reacting the 2-mercaptobenz-oxazole or -thiazole with a compound of formula (IV)

$$CF_2=CH-CH_2-CH_2-L \qquad (IV)$$

wherein L is a good leaving group.

7 Claims, No Drawings

PROCESS FOR PREPARING NEMATICIDAL BENZOXAZOLE AND BENZTHIAZOLE COMPOUNDS

This invention relates to a chemical process for the preparation of compounds useful as nematicides, and to intermediates of use in the process.

In United Kingdom Patent Publication No. 2270689 we have disclosed a series of nematicidal 2-(4,4-difluoro-but-3-enylthio)-benzoxazoles and benzthiazoles, and methods of preparing them. The present application relates to an improved method for preparing nematicidal 2-(4,4-difluoro-but-3-enylthio)-benzoxazoles and benzthiazoles.

According to the present invention there is provided a process for the preparation of a compound of formula (I)

wherein $R^1$, $R^2$, $R^3$, and $R^4$ are each independently hydrogen, optionally substituted alkyl, optionally substituted alkenyl, alkynyl, cycloalkyl, alkylcycloalkyl, optionally substituted aryl, optionally substituted arylalkyl, optionally substituted aryloxy, optionally substituted arylalkoxy, alkoxy, alkenyloxy, alkynyloxy, hydroxyalkyl, alkoxyalkyl, alkylthio, alkenylthio, alkynylthio, haloalkyl, haloalkenyl, haloalkynyl, haloalkoxy, haloalkenyloxy, haloalkynyloxy, haloalkylthio, haloalkenylthio, haloalkynylthio, halogen, hydroxy, cyano, nitro, $-NR^5R^6$, $-NR^7COR^8$, $-NR^7CSR^8$, $-NR^9SO_2R^{10}$, $-N(SO_2-R^{11})$, $-(SO_2-R^{12})$, $-COR^{13}$, $-CONR^{14}R^{15}$, $-COOR^{16}$, $-OCOR^{17}$, $-OSO_2R^{18}$, $-SO_2NR^{19}R^{20}$, $-SO_2R^{21}$, $-SOR^{22}$, $-CSNR^{23}R^{24}$, $-SiR^{25}R^{26}R^{27}$, $-OCH_2CO_2R^{28}$, $-OCH_2CH_2CO_2R^{29}$, $-SO_2Z$, $-CONR^{30}SO_2R^{31}$, $-NHCONR^{32}R^{33}$, $-NHCSNR^{32}R^{33}$ or an adjacent pair of $R^1$, $R^2$, $R^3$ and $R^4$ when taken together form a fused 5- or 6-membered carbocyclic or heterocyclic ring; $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$ and $R^{33}$ are each independently selected from hydrogen, alkyl, alkenyl, alkynyl, haloalkyl, haloalkenyl, haloalkynyl, optionally substituted aryl and optionally substituted arylalkyl; Z is halogen; and X is oxygen or sulphur, which comprises (a) reacting a substituted ortho-nitro or -nitroso phenol or a substituted ortho-nitro or -nitroso thiophenol of formula (II), wherein $R^1$–$R^4$ and X have the values previously defined, and y is 1 or 2, with a reducing agent comprising an alkali metal dithionite in an alkaline reaction medium in the presence of carbon disulphide, to form the substituted 2-mercaptobenzoxazole or -thiazole of formula (III) wherein $R^1$–$R^4$ and X have the values previously defined, acidifying the reaction mixture and collecting the 2-mercaptobenzoxazole or -thiazole; and (b) reacting the 2-mercaptobenz-oxazole or -thiazole (III), with a compound of formula (IV) wherein L is a good leaving group to form the compound of formula (I).

Preferably the reducing agent is sodium, potassium or caesium dithionite. Sodium diothionite is especially preferred.

The alkaline reaction medium is preferably an aqueous alcoholic solution of an alkali metal hydroxide, for example a solution of sodium or potassium hydroxide in methanol or ethanol containing water (e.g. methanol or ethanol containing about 5 to about 15% by volume of water). The reaction temperature at atmospheric pressure is preferably from room temperature up to about 80° C.

The reaction of the 2-mercaptobenz-oxazole or -thiazole (III) with the compound of formula (IV) is carried out under conditions well known in the art for such displacement reactions, for example in the presence of a mild base such as an alkali metal carbonate, for example potassium or sodium carbonate, in an inert solvent, at a temperature in the range from about 40° C. to about 100° C. at atmospheric pressure, and conveniently at the reflux temperature of a suitable inert solvent such as acetone, which has a boiling point within this range.

The group L in compound (IV) may be for example an $OSO_2R^a$ group wherein $R^a$ is a $C_{1-4}$ alkyl group, or a phenyl group optionally substituted with a $C_{1-4}$ alkyl group, for example para-tolyl, or it may preferably be a halogen atom, such as chlorine, bromine and iodine. Bromine is especially preferred.

When any one of $R^1$ to $R^4$ is a substituted alkyl group, the substituent or substituents may comprise nitro; cyano; alkoxyimino, wherein the alkoxy group preferably has 1 to 6 carbon atoms; alkoxycarbonyl of 2 to 4 carbon atoms; carbamoyl; mono- or di-alkylcarbamoyl wherein the one or two alkyl groups preferably each have from 1 to 6 carbon atoms; amino; mono- or di-alkylamino wherein the one or two alkyl groups each preferably have from 1 to 6 carbon atoms; acylamido wherein the acyl group is formyl or an alkylcarbonyl group of 2 to 6 carbon atoms; alkanesulphonyl preferably of 1 to 6 carbon atoms; or arylsulphonyl, for example benzenesulphonyl, optionally substituted by halogen, $C_{1-4}$ alkoxy or nitro.

When any one of $R^1$ to $R^4$ is a substituted alkenyl group, the substituent or substituents may comprise for example nitro or cyano.

When any one of $R^1$ to $R^{33}$ is an alkyl group it may be straight or branched chain and is preferably $C_{1-6}$ alkyl, and in particular $C_{1-4}$ alkyl, for example methyl, ethyl, propyl, iso-propyl, n-butyl, iso-butyl, sec-butyl or t-butyl.

When any one of $R^1$ to $R^{33}$ is an alkenyl or alkynyl group it may be straight or branched chain and is preferably $C_{2-6}$ alkenyl or $C_{2-6}$ alkynyl, for example vinyl, allyl, but-3-enyl, 3-methyl-but-3-enyl, ethynyl or propargyl.

When any one of $R^1$ to $R^4$ is a cycloalkyl or alkylcycloalkyl group, it is preferably $C_{3-6}$ cycloalkyl or $C_{4-7}$ alkylcycloalkyl, for example cyclopropyl, cyclopentyl, cyclohexyl or methylcyclopropyl.

When any one of $R^1$ to $R^{33}$ is an optionally substituted aryl or an optionally substituted arylalkyl group, it is preferably an optionally substituted phenyl group or an optionally substituted phenyl-$C_{1-2}$-alkyl group, wherein the preferred optional substitution is one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example phenyl, benzyl, 4-methylphenyl, 4-chlorophenyl, 4-fluorophenyl, 4-nitrophenyl, 3-trifluoromethylphenyl, 4-trifluoromethylphenyl, 4-chlorobenzyl, 4-fluorobenzyl, 3-trifluoromethylbenzyl, 4-trifluoromethylbenzyl, 4-nitrobenzyl or 4-methylbenzyl.

When any one of $R^1$ to $R^4$ is an optionally substituted aryloxy or an optionally substituted arylalkoxy group, it is preferably optionally substituted phenoxy or optionally substituted phenyl-$C_{1-2}$-alkoxy, group, wherein the preferred optional substitution is one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example phenoxy, benzoxy, 4-methylphenoxy, 4-chlorophenoxy, 4-fluorophenoxy, 4-nitrophenoxy, 3-trifluoromethylphenoxy, 4-trifluoromethylphenoxy 4-chlorobenzoxy, 4-fluorobenzoxy, 3-trifluoromethylbenzoxy, 4-trifluoromethylbenzoxy, 4-nitrobenzoxy or 4-methylbenzoxy.

When any one of $R^1$ to $R^{33}$ is a haloalkyl, haloalkenyl or haloalkynyl group, it may contain one or more halogen atoms selected from chlorine, fluorine or bromine, and the alkyl, alkenyl or alkynyl moiety may be straight or branched chain and is preferably $C_{1-6}$ alkyl, especially $C_{1-4}$ alkyl, $C_{2-6}$ alkenyl or $C_{2-6}$ alkynyl, for example, fluoromethyl, difluoromethyl, trifluoromethyl, chloromethyl, dichloromethyl, trichloromethyl, 2-fluoroethyl, 2,2,2-trifluoroethyl, pentafluoroethyl, 2,2-difluoroethenyl, 3,3-dichloroprop-2-enyl, 2-chloroprop-2-enyl, 3,4,4-trifluorobut-3-enyl, 4-fluorobut-3-enyl, 4,4-difluorobut-3-enyl or 3-methyl-4,4-difluorobut-3-enyl.

When any one of $R^1$ to $R^4$ is an alkoxy, alkenyloxy, alkynyloxy or alkoxyalkyl group, it may be straight or branched chain and is preferably $C_{1-6}$ alkoxy, for example methoxy, ethoxy, n-propoxy, iso-propoxy, n-butoxy, iso-butoxy, sec-butoxy or t-butoxy, $C_{2-6}$ alkenyloxy, for example vinyloxy, allyloxy, but-3-enyloxy or 3-methylbut-3-enyloxy, $C_{2-6}$ alkynyloxy, for example propargyloxy, $C_{2-6}$ alkoxyalkyl, for example methoxymethyl, methoxyethyl or ethoxymethyl, or $C_{3-6}$ dialkoxyalkyl, for example dimethoxymethyl or diethoxymethyl.

When any one of $R^1$ to $R^4$ is a haloalkoxy group, a haloalkenyloxy group or a haloalkynyloxy group, it may contain one or more halogen atoms selected from chlorine, fluorine or bromine, and the alkoxy, alkenyloxy or alkynyloxy moiety may be straight or branched chain and is preferably $C_{1-6}$ alkoxy, $C_{2-6}$ alkenyloxy or $C_{2-6}$ alkynyloxy, for example, trichloromethoxy, fluoromethoxy, difluoromethoxy, trifluoromethoxy, 2-fluoroethoxy, 2,2,2-trifluoroethoxy, pentafluoroethoxy, 1,1,2,2-tetrafluoroethoxy, 2,2-difluoroethenyloxy, 3,4,4-trifluorobut-3-enyloxy, 4-fluorobut-3-enyloxy, 4,4-difluorobut-3-enyloxy, 3-methyl-4,4-difluorobut-3-enyloxy, 2-chloroprop-2-enyloxy or 3,3-dichloroprop-2-enyloxy.

When any one of $R^1$ to $R^4$ is an alkylthio group, an alkenylthio group or an alkynylthio group, the alkyl, alkenyl or alkynyl moiety is preferably $C_{1-6}$ alkyl, especially $C_{1-4}$ alkyl, $C_{2-6}$ alkenyl or $C_{2-6}$ alkynyl, for example methylthio, ethylthio, n-propylthio, iso-propylthio, n-butylthio, iso-butylthio, sec-butylthio, t-butylthio, allylthio, but-3-enylthio, 3-methylbut-3-enylthio or propargylthio.

When any one of $R^1$ to $R^4$ is a haloalkylthio group, a haloalkenylthio group or a haloalkynylthio group, it may contain one or more halogen atoms selected from chlorine, fluorine or bromine, and the alkyl, alkenyl or alkynyl moiety is preferably $C_{1-6}$ alkyl, especially $C_{1-4}$ alkyl, $C_{2-6}$ alkenyl or $C_{2-6}$ alkynyl, for example fluoromethylthio, difluoromethylthio, trifluoromethylthio, trichloromethylthio, 2-fluoroethylthio, 2,2,2-trifluoroethylthio, 3-fluoro-n-propylthio, pentafluoroethylthio, 2-chloroprop-2-enylthio, 3,3-dichloroprop-2-enylthio, 3,4,4-trifluorobut-3-enylthio, 4-fluorobut-3-enylthio, 4,4-difluorobut-3-enylthio or 3-methyl-4,4-difluorobut-3-enylthio.

When any one of $R^1$ to $R^4$ is halogen, it is preferably fluorine, chlorine, bromine or iodine.

When any one of $R^1$ to $R^4$ is the group —$NR_5R_6$, it is preferably —$NH_2$, a $C_{1-6}$ alkylamino group, for example methylamino or ethylamino, or a di-($C_{1-6}$ alkyl)-amino group, for example dimethylamino or diethylamino.

When any one of $R^1$ to $R^4$ is the group —$NR^7COR^8$ it is preferably, —NHCHO, a $C_{2-6}$ acylamino group or an optionally substituted benzamido group, for example —$NHCOCH_3$, —$NHCOC_2H_5$, benzamido or benzamido optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro.

When any one of $R^1$ to $R^4$ is the group —$NR^7CSR^8$, $R^7$ and $R^8$ are preferably each independently a $C_{1-6}$ alkyl group.

When any one of $R^1$ to $R^4$ is the group —$NR^9SO_2R^{10}$ it is preferably a $C_{1-6}$ alkanesulphonamido group, for example —$NHSO_2CH_3$ or —$NHSO_2C_2H_5$.

When any one of $R^1$ to $R^4$ is the group —$N(SO_2R^{11})$-$(SO_2R^{12})$ it is preferably a di-($C_{1-6}$ alkanesulphonyl)amino group, for example —$N(SO_2CH_3)_2$ or —$N(SO_2C_2H_5)_2$.

When any one of $R^1$ to $R^4$ is the group —$COR^{13}$, it is preferably formyl, a $C_{2-6}$ acyl group or an optionally substituted benzoyl group, for example acetyl, propionyl, n-butanoyl, benzoyl or benzoyl optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example 4-chlorobenzoyl, 4-fluorobenzoyl, 4-bromobenzoyl, 4-methylbenzoyl or 4-trifluoromethylbenzoyl.

When any one of $R^1$ to $R^4$ is the group —$CONR^{14}R^{15}$, it is preferably —$CONH_2$, an N—($C_{1-6}$ alkyl)-carboxamido group, for example —$CONHCH_3$, —$CONHC_2H_5$ or —$CONHCH_2CH_2CH_3$, or an N,N-di-($C_{1-6}$ alkyl)-carboxamido group, for example —$CON(CH_3)_2$, —$CON(CH_3)(C_2H_5)$ or —$CON(C_2H_5)_2$.

When any one of $R^1$ to $R^3$ is the group —$COOR^{16}$, it is preferably —COOH, a $C_{1-6}$ alkoxycarbonyl group, for example methoxycarbonyl or ethoxycarbonyl, or a $C_{2-6}$ haloalkenyloxycarbonyl group, for example 3,4,4-trifluorobut-3-enyloxycarbonyl, 4-fluorobut-3-enyloxycarbonyl, 4,4-difluorobut-3-enyloxycarbonyl or 3-methyl-4,4-difluorobut-3-enyloxycarbonyl, When any one of $R^1$ to $R^4$ is the group —$OCOR^{17}$, it is preferably a $C_{2-6}$ acyloxy group or an optionally substituted benzoyloxy, for example —$OCOCH_3$, —$OCOC_2H_5$, benzoyloxy or benzoyloxy optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro.

When any one of $R^1$ to $R^4$ is the group —$OSO_2R^{18}$, it is preferably a $C_{1-6}$ alkanesulphonyloxy group or an optionally substituted benzenesulphonyloxy group, for example methanesulphonyloxy, ethanesulphonyloxy, benzenesulphonyloxy or benzenesulphonyloxy optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example 4-methylbenzenesulphonyloxy.

When any one of $R^1$ to $R^4$ is the group —$SO_2NR^{19}R^{20}$, it is preferably —$SO_2NH_2$, a $C_{1-6}$ alkylaminosulphonyl group, for example —$SO_2NHCH_3$ or —$SO_2NHC_2H_5$, or a di-($C_{1-6}$ alkyl)-aminosulphonyl group, for example —$SO_2N(CH_3)_2$ or —$SO_2N(C_2H_5)_2$.

When any one of $R^1$ to $R^4$ is the group —$SO_2R^{21}$, it is preferably a $C_{1-6}$ alkanesulphonyl group, a $C_{1-6}$ haloalkanesulphonyl group or an optionally substituted benzenesulphonyl group, for example methanesulphonyl, ethanesulphonyl, trifluoromethanesulphonyl, benzenesulphonyl or benzenesulphonyl optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example 4-methylbenzenesulphonyl.

When any one of $R^1$ to $R^4$ is the group —$SOR^{22}$, it is preferably a $C_{1-6}$ alkanesulphinyl group, for example methanesulphinyl or ethanesulphinyl, or a $C_{1-6}$ haloalkanesulphinyl group, for example trifluoromethanesulphinyl.

When any one of $R^1$ to $R^4$ is the group —$CSNR^{23}R^{24}$ it is preferably —$CSNH_2$, —$CSNHCH_3$ or —$CSN(CH_3)_2$.

When any one of $R^1$ to $R^4$ is the group —$SiR^{25}R^{26}R^{27}$, it is preferably a tri-($C_{1-6}$ alkyl)silyl group, for example, trimethylsilyl or triethylsilyl.

When any one of $R^1$ to $R^4$ is the group —$OCH_2CO_2R^{28}$, it is preferably a $C_{1-6}$ alkoxycarbonylmethoxy group, for example methoxycarbonylmethoxy or ethoxycarbonylmethoxy.

When any one of $R^1$ to $R^4$ is the group —$OCH_2CH_2CO_2R^{29}$, it is preferably a $C_{1-6}$ alkoxycarbonylethoxy group, for example methoxycarbonylethoxy or ethoxycarbonylethoxy.

When any one of $R^1$ to $R^4$ is the group —$CONR^3{}_0SO_2R^{31}$, it is preferably an N-($C_{1-6}$ alkanesulphonyl)-carboxamido group or an N-($C_{1-6}$ alkyl)-N-($C_{1-6}$ alkanesulphonyl)carboxamido group, for example N-(methanesulphonyl)-carboxamido or N-methyl-N-(methanesulphonyl)carboxamido.

When any one of $R^1$ to $R^4$ is the group —$NHCONR^{32}R^{33}$ or —$NHCSNR^{32}R^{33}$, $R^{32}$ and $R^{33}$ are preferably each independently a $C_{1-6}$ alkyl group.

When any one of $R^1$ to $R^4$ is the group —$SO_2Z$, it is preferably —$SO_2F$, —$SO_2Br$ or $SO_2Cl$.

When an adjacent pair of $R^1$, $R^2$, $R^3$ and $R^4$ taken together form a fused 5- or 6-membered carbocyclic or heterocyclic ring, the pair of substituents taken together is preferably —$(CH_2)_3$—, —$(CH_2)_4$—, —CH=CH—CH=CH—, —O—$CH_2$—O— optionally substituted with one or two halogen atoms, for example —O—CHF—O— or —O—$CF_2$—O—, —O—CH($CH_3$)—O—, —O—C($CH_3$)$_2$—O— or —O—$(CH_2)_2$—O—, and the fused ring formed thereby is preferably a 5- or 6-membered heterocyclic ring containing two oxygen atoms and optionally substituted with one or more halogen or methyl groups, or a 5- or 6-membered carbocyclic ring.

Of particular interest are compounds of formula (I) where $R^1$ to $R^4$ are each independently hydrogen, fluorine, chlorine, methyl, ethyl, methoxy, ethoxy, trifluoromethyl, trifluoromethoxy, trifluoroethoxy, $SCH_3$ and $SCH_2CF_3$.

The nematicidal properties of compounds of formula (I) and oxidised derivatives thereof are described in UK Patent Publication No. 2270689.

Examples of the compounds of formula (I) which may be prepared according to the process of the invention are set out in Table I.

TABLE I

| COMPOUND NO. | $R^1$ | $R^2$ | $R^3$ | $R^4$ | X |
|---|---|---|---|---|---|
| 1 | H | H | H | H | S |
| 2 | H | H | H | H | O |
| 3 | H | F | H | H | O |
| 4 | H | H | F | H | S |
| 5 | $NO_2$ | H | H | H | O |
| 6 | $NH_2$ | H | H | H | O |
| 7 | $CH_3$ | H | H | H | S |
| 8 | H | F | F | H | O |
| 9 | H | H | H | H | O |
| 10 | $CO_2CH_3$ | H | H | H | O |
| 11 | $NHCOCH_3$ | H | H | H | S |
| 12 | H | H | H | H | S |
| 13 | COOH | H | H | H | S |
| 14 | H | H | H | H | O |
| 15 | F | H | H | H | S |
| 16 | H | H | H | $CH_3$ | S |
| 17 | H | H | $CH_3$ | H | O |
| 18 | H | H | $CH_2CH=CH_2$ | H | O |
| 19 | H | H | $^cC_3H_5$ | H | O |
| 20 | H | H | Cl | H | O |
| 21 | H | H | CN | H | S |
| 22 | H | $CH_3$ | H | H | S |

TABLE I-continued

| COMPOUND NO. | $R^1$ | $R^2$ | $R^3$ | $R^4$ | X |
|---|---|---|---|---|---|
| 23 | H | CH$_2$CH=CH$_2$ | H | H | O |
| 24 | H | $^c$C$_3$H$_5$ | H | H | O |
| 25 | H | Cl | H | H | S |
| 26 | H | C$_6$H$_5$ | H | H | O |
| 27 | CH$_3$ | CH$_3$ | H | H | O |
| 28 | Cl | Cl | H | H | S |
| 29 | F | Cl | H | H | O |
| 30 | OCH$_3$ | H | NHCOCH$_3$ | H | O |
| 31 | OCH$_3$ | H | OCH$_3$ | H | O |
| 32 | OCH$_3$ | OCH$_3$ | H | H | O |
| 33 | 1-CH$_3$—$^c$C$_3$H$_5$ | H | H | H | S |
| 34 | OH | F | H | H | O |
| 35 | OH | H | Cl | H | S |
| 36 | H | H | CO$_2$CH$_3$ | H | O |
| 37 | OCH$_2$CF$_3$ | H | H | H | S |
| 38 | OCH$_2$CF$_3$ | H | H | H | O |
| 39 | OCH$_2$CH$_3$ | H | H | H | S |
| 40 | H | H | CH$_2$OCH$_3$ | H | S |
| 41 | H | CH$_3$ | H | H | O |
| 42 | H | H | CN | H | O |
| 43 |  | —CH=CH—CH=CH— | H | H | S |
| 44 |  | —CH=CH—CH=CH— | H | H | O |
| 45 | Cl | H | H | H | O |
| 46 | Cl | H | H | H | S |
| 47 | F | H | H | H | O |
| 48 | CH$_3$ | H | H | H | O |
| 49 | NHCOCH$_3$ | H | H | H | O |
| 50 | NHCOC$_2$H$_5$ | H | H | H | S |
| 51 | NHSO$_2$CH$_3$ | H | H | H | S |
| 52 | NO$_2$ | H | H | H | S |
| 53 | N(SO$_2$CH$_3$)$_2$ | H | H | H | O |
| 54 | OH | H | H | H | O |
| 55 | OCOCH$_3$ | H | H | H | O |
| 56 | OCH$_2$CH$_3$ | H | H | H | O |
| 57 | OCH$_3$ | H | H | H | O |
| 58 | OCH$_3$ | H | H | H | S |
| 59 | OCH$_3$ | H | H | Cl | S |
| 60 | OSO$_2$CH$_3$ | H | H | H | O |
| 61 | H | Br | H | H | S |
| 62 | H | CF$_3$ | H | H | S |
| 63 | H | Cl | H | H | S |
| 64 | H | CO$_2$CH$_2$CH$_2$CH=CF$_2$ | H | H | S |
| 65 | H | CONH$_2$ | H | H | S |
| 66 | H | CONHCH$_2$CH$_2$CH$_3$ | H | H | S |
| 67 | H | CON(CH$_3$)$_2$ | H | H | S |
| 68 | H | COOH | H | H | S |
| 69 | H | F | H | H | S |
| 70 | H | NHCOC$_6$H$_5$ | H | H | S |
| 71 | H | OCH$_3$ | H | H | S |
| 72 | H | SCH$_3$ | H | H | S |
| 73 | H | SO$_2$C$_2$H$_5$ | H | H | O |
| 74 | H | SO$_2$CH$_3$ | H | H | O |
| 75 | H | SO$_2$N(C$_2$H$_5$)$_2$ | H | H | O |
| 76 | H | SO$_2$N(CH$_3$)$_2$ | H | H | S |
| 77 | H | H | Cl | H | S |
| 78 | H | H | F | H | O |
| 79 | H | H | H | CH$_3$ | O |
| 80 | H | H | H | NH | O |
| 81 | H | H | H | NO$_2$ | O |
| 82 | H | H | H | OH | O |
| 83 | H | H | H | OCH$_2$CH$_2$F | O |
| 84 | COOH | H | H | H | O |
| 85 | NHCHO | H | H | H | O |
| 86 | SCH$_3$ | H | H | H | S |
| 87 | H | Br | H | H | S |
| 88 | H | Br | H | H | S |
| 89 | H | Cl | H | H | O |
| 90 | H | CN | H | H | O |
| 91 | H | CN | H | H | S |
| 92 | H | CO$_2$CH$_2$CH$_2$CH=CF$_2$ | H | H | S |
| 93 | H | CO$_2$CH$_2$CH$_2$CH=CF$_2$ | H | H | S |
| 94 | H | COOH | H | H | O |
| 95 | H | F | H | H | S |
| 96 | H | OCF$_3$ | H | H | S |
| 97 | H | H | H | COOH | O |
| 98 | H | H | H | NHCOC$_2$H$_5$ | O |
| 99 | H | H | H | NHSO$_2$CH$_3$ | O |
| 100 | H | H | H | OCOC$_2$H$_5$ | O |
| 101 | H | H | H | OCOCH$_2$CH$_2$CH=CF$_2$ | O |
| 102 | H | H | H | OCH$_3$ | O |

TABLE I-continued

| COMPOUND NO. | R$^1$ | R$^2$ | R$^3$ | R$^4$ | X |
|---|---|---|---|---|---|
| 103 | H | NH$_2$ | H | H | O |
| 104 | OCH$_2$CCl=CH2 | H | H | H | O |
| 105 | OCH$_2$CH=CCl$_2$ | H | H | H | O |
| 106 | OCH$_2$CO$_2$C$_2$H$_5$ | H | H | H | O |
| 107 | CN | H | H | H | O |
| 108 | CONH$_2$ | H | H | H | O |
| 109 | CON(CH$_3$)C$_2$H$_5$ | H | H | H | O |
| 110 | OCH$_2$CH$_2$F | H | H | H | O |
| 111 | OCH$_2$CH$_2$CH$_3$ | H | H | H | O |
| 112 | OCH(CH$_3$)C$_2$H$_5$ | H | H | H | O |
| 113 | H | SCH$_3$ | H | H | O |
| 114 | H | H | NO$_2$ | H | O |
| 115 | H | NO$_2$ | NO$_2$ | H | O |
| 116 | H | CF$_3$ | H | H | O |
| 117 | H | H | H | H | S |
| 118 | H | CO$_2$CH$_2$CH$_2$CH=CF$_2$H | H | O | |
| 119 | H | H | H | NHCOCF$_3$ | O |
| 120 | SO$_2$NH$_2$ | H | H | H | S |
| 121 | H | SOCH$_3$ | H | H | S |
| 122 | H | CONHCH$_3$ | H | H | S |
| 123 | H | SO$_2$NHCH$_3$ | H | H | S |
| 124 | H | SO$_2$C$_2$H$_5$ | H | H | S |
| 125 | H | CSNH$_2$ | H | H | S |
| 126 | H | NO$_2$ | H | H | S |
| 127 | H | H | NO$_2$ | H | S |
| 128 | —O—CH$_2$—O— | | H | S | |
| 129 | SO$_2$F | H | H | H | S |
| 130 | H | H | H | OCH$_3$ | S |
| 131 | OCH$_3$ | OCH$_3$ | H | H | S |
| 132 | H | C≡CH | H | H | S |
| 133 | H | SO$_2$CF$_3$ | H | H | S |
| 134 | NHCOC$_6$H$_5$ | H | H | H | S |
| 135 | H | H | H | Cl | S |
| 136 | H | H | Br | H | S |
| 137 | H | SCF$_3$ | H | H | S |
| 138 | H | SOCF$_3$ | H | H | S |
| 139 | H | COCH$_3$ | H | H | S |
| 140 | H | SCH$_2$CH$_2$CH$_3$ | H | H | S |
| 141 | H | I | H | H | S |
| 142 | H | * | H | | O |
| | ** indicates a fused —CH=CH—CH=CH— link | | | | |
| 143 | H | NO$_2$ | H | H | O |
| 144 | H | H | H | CONHCH$_2$C$_6$H$_5$ | O |
| 145 | H | CONH$_2$ | H | H | O |
| 146 | H | CO$_2$CH$_3$ | H | H | O |
| 147 | OCH$_2$CH=CH$_2$ | H | H | H | O |
| 148 | NH$_2$ | H | H | H | S |
| 149 | H | OH | H | H | O |
| 150 | H | SCF$_3$ | H | H | S |
| 151 | H | SCF$_3$ | H | H | S |
| 152 | H | H | H | CO$_2$CH$_3$ | O |
| 153 | H | CO$_2$CH$_2$CH$_2$F | H | H | O |
| 154 | I | H | H | H | S |
| 155 | C≡CH | H | H | H | S |
| 156 | H | OCH$_3$ | H | H | O |
| 157 | H | F | H | H | S |
| 158 | H | CONHCH$_2$C$_6$H$_5$ | H | H | O |
| 159 | OCH$_2$CH$_2$CH=CF$_2$ | H | H | H | O |
| 160 | NO$_2$ | H | H | H | S |
| 161 | NO$_2$ | H | H | H | S |
| 162 | —O—CH$_2$—O— | | H | H | O |
| 163 | —CH=CH—CH=CH— | | H | H | O |
| 164 | —CH=CH—CH=CH— | | H | H | S |
| 165 | 1—CH$_3$$^c$C$_3$H$_5$ | H | H | H | O |
| 166 | Br | H | H | H | O |
| 167 | Br | H | H | H | S |
| 168 | C≡CH | H | H | H | O |
| 169 | C$_6$H$_5$ | H | H | H | O |
| 170 | C$_6$H$_5$ | H | H | H | S |
| 171 | $^c$C$_3$H$_5$ | H | H | H | O |
| 172 | $^c$C$_3$H$_5$ | H | H | H | S |
| 173 | CF$_2$H$_2$ | H | H | H | O |
| 174 | CF$_2$H$_2$ | H | H | H | S |
| 175 | CF$_3$ | H | H | H | O |
| 176 | CF$_3$ | H | H | H | S |
| 177 | CH$_2$CH=CH$_2$ | H | H | H | O |
| 178 | CH$_2$CH=CH$_2$ | H | H | H | S |
| 179 | CH$_2$CH$_2$F | H | H | H | O |
| 180 | CH$_2$CH$_2$F | H | H | H | S |
| 181 | CH$_2$CH$_3$ | H | H | H | O |

TABLE I-continued

| COMPOUND NO. | R¹ | R² | R³ | R⁴ | X |
|---|---|---|---|---|---|
| 182 | CH₂CH₃ | H | H | H | S |
| 183 | CH₂OH | H | H | H | O |
| 184 | CH₂OH | H | H | H | S |
| 185 | CH₃ | CH₃ | H | H | S |
| 186 | CH₃ | H | H | H | O |
| 187 | CH₃ | H | H | H | O |
| 188 | CH₃ | H | H | H | S |
| 189 | CH₃ | H | H | H | S |
| 190 | Cl | Cl | H | H | O |
| 191 | Cl | H | H | H | O |
| 192 | Cl | H | H | H | S |
| 193 | CN | H | H | H | S |
| 194 | CO₂CH₂CH₂CH=CF₂ | H | H | H | O |
| 195 | CO₂CH₂CH₂CH=CF₂ | H | H | H | O |
| 196 | CO₂CH₂CH₂CH=CF₂ | H | H | H | O |
| 197 | CO₂CH₂CH₂CH=CF₂ | H | H | H | S |
| 198 | CO₂CH₂CH₂CH=CF₂ | H | H | H | S |
| 199 | CO₂CH₂CH₂CH=CF₂ | H | H | H | S |
| 200 | CO₂CH₂CH₂F | H | H | H | O |
| 201 | CO₂CH₂CH₂F | H | H | H | S |
| 202 | CO₂CH₃ | H | H | H | O |
| 203 | CO₂CH₃ | H | H | H | O |
| 204 | CO₂CH₃ | H | H | H | S |
| 205 | CO₂CH₃ | H | H | H | S |
| 206 | CO₂CH₃ | H | H | H | S |
| 207 | COCH₃ | H | H | H | O |
| 208 | COCH₃ | H | H | H | S |
| 209 | CON(CH₃)₂ | H | H | H | O |
| 210 | CON(CH₃)₂ | H | H | H | S |
| 211 | CON(CH₃)C₂H₅ | H | H | H | S |
| 212 | CONH₂ | H | H | H | H |
| 213 | CONHCH₂C₆H₅ | H | H | H | O |
| 214 | CONHCH₂C₆H₅ | H | H | H | S |
| 215 | CONHCH₂CH₂CH=CF₂ | H | H | H | O |
| 216 | CONHCH₂CH₂CH=CF₂ | H | H | H | S |
| 217 | CONHCH₂CH₂CH₃ | H | H | H | O |
| 218 | CONHCH₂CH₂CH₃ | H | H | H | S |
| 219 | CONHCH₃ | H | H | H | O |
| 220 | CONHCH₃ | H | H | H | S |
| 221 | CONHSO₂CH₃ | H | H | H | O |
| 222 | CONHSO₂CH₃ | H | H | H | S |
| 223 | COSCH₂CH₂CH=CF₂ | H | H | H | O |
| 224 | COSCH₂CH₂CH=CF₂ | H | H | H | S |
| 225 | CSNH₂ | H | H | H | O |
| 226 | CSNH₂ | H | H | H | S |
| 227 | F | Cl | H | H | S |
| 228 | I | H | H | H | O |
| 229 | I | H | H | H | O |
| 230 | I | H | H | H | S |
| 231 | N(SO₂CH₃)₂ | H | H | H | S |
| 232 | NHCHO | H | H | H | S |
| 233 | NHCOC₂H₅ | H | H | H | O |
| 234 | NHCOC₆H₅ | H | H | H | O |
| 235 | NHSO₂CH₃ | H | H | H | O |
| 236 | NO₂ | H | H | H | O |
| 237 | NO₂ | H | H | H | O |
| 238 | OCF₂CF₂H | H | H | H | O |
| 239 | OCF₂CF₂H | H | H | H | S |
| 240 | OCF₂H | H | H | H | O |
| 241 | OCF₂H | H | H | H | O |
| 242 | OCF₂H | H | H | H | O |
| 243 | OCF₂H | H | H | H | S |
| 244 | OCF₂H | H | H | H | S |
| 245 | OCF₂H | H | H | H | S |
| 246 | OCF₃ | H | H | H | O |
| 247 | OCF₃ | H | H | H | S |
| 248 | OCH(CH₃)C₂H₅ | H | H | H | S |
| 249 | OCH₂CCl=CH₂ | H | H | H | S |
| 250 | OCH₂CF₃ | H | H | H | O |
| 251 | OCH₂CF₃ | H | H | H | S |
| 252 | OCH₂CH=CCl₂ | H | H | H | S |
| 253 | OCH₂CH=CH₂ | H | H | H | S |
| 254 | OCH₂CH₂CH=CF₂ | H | H | H | S |
| 255 | OCH₂CH₂CH₃ | H | H | H | S |
| 256 | OCH₂CH₂F | H | H | H | S |
| 257 | OCH₂CH₃ | H | H | H | O |
| 258 | OCH₂CH₃ | H | H | H | O |
| 259 | OCH₂CO₂C₂H₅ | H | H | H | S |
| 260 | OCH₃ | H | H | Cl | O |
| 261 | OCH₃ | H | NHCOCH₃ | H | S |

TABLE I-continued

| COMPOUND NO. | R¹ | R² | R³ | R⁴ | X |
|---|---|---|---|---|---|
| 262 | OCH₃ | H | OCH₃ | H | S |
| 263 | OCOCH₃ | H | H | H | S |
| 264 | OH | F | H | H | S |
| 265 | OH | H | Cl | H | O |
| 266 | OH | H | H | H | S |
| 267 | OSO₂CH₃ | H | H | H | S |
| 268 | SCF₃ | H | H | H | O |
| 269 | SCF₃ | H | H | H | S |
| 270 | SCH₂CH₂CH₃ | H | H | H | O |
| 271 | SCH₂CH₂CH₃ | H | H | H | S |
| 272 | SCH₃ | H | H | H | O |
| 273 | SO₂C₂H₅ | H | H | H | O |
| 274 | SO₂C₂H₅ | H | H | H | S |
| 275 | SO₂CF₃ | H | H | H | O |
| 276 | SO₂CF₃ | H | H | H | S |
| 277 | SO₂CH₃ | H | H | H | O |
| 278 | SO₂CH₃ | H | H | H | S |
| 279 | SO₂F | H | H | H | O |
| 280 | SO₂N(C₂H₅)₂ | H | H | H | O |
| 281 | SO₂N(C₂H₅)₂ | H | H | H | S |
| 282 | SO₂N(CH₃)₂ | H | H | H | O |
| 283 | SO₂N(CH₃)₂ | H | H | H | S |
| 284 | SO₂NH₂ | H | H | H | O |
| 285 | SO₂NHCH₃ | H | H | H | O |
| 286 | SO₂NHCH₃ | H | H | H | S |
| 287 | SOCF₃ | H | H | H | O |
| 288 | SOCF₃ | H | H | H | S |
| 289 | SOCH₃ | H | H | H | O |
| 290 | SOCH₃ | H | H | H | S |
| 291 | H | ** | H | | S |
| | | indicates a fused —CH=CH—CH=CH— link | | | |
| 292 | H | 1—CH₃—ᶜC₃H₅ | H | H | O |
| 293 | H | 1—CH₃—ᶜC₃H₅ | H | H | |
| 294 | H | Br | H | H | O |
| 295 | H | Br | H | H | O |
| 296 | H | Br | H | H | O |
| 297 | H | C≡CH | H | H | O |
| 298 | H | C₆H₅ | H | H | S |
| 299 | H | ᶜC₃H₅ | H | H | S |
| 300 | H | CF₂H₂ | H | H | O |
| 301 | H | CF₂H₂ | H | H | S |
| 302 | H | CH₂CH=CH₂ | H | H | S |
| 303 | H | CH₂CH₂F | H | H | O |
| 304 | H | CH₂CH₂F | H | H | S |
| 305 | H | CH₂CH₃ | H | H | O |
| 306 | H | CH₂CH₃ | H | H | S |
| 307 | H | CH₂OH | H | H | O |
| 308 | H | CH₂OH | H | H | S |
| 309 | H | CHO | H | H | O |
| 310 | H | CHO | H | H | S |
| 311 | H | Cl | H | H | O |
| 312 | H | CO₂CH₂CH₂CH=CF₂H | H | O | |
| 313 | H | CO₂CH₂CH₂CH=CF₂H | H | O | |
| 314 | H | CO₂CH₂CH₂F | H | H | S |
| 315 | H | CO₂CH₂CH₃ | H | H | O |
| 316 | H | CO₂CH₂CH₃ | H | H | S |
| 317 | H | CO₂CH₃ | H | H | S |
| 318 | H | COCH₃ | H | H | O |
| 319 | H | CON(CH₃)₂ | H | H | O |
| 320 | H | CON(CH₃)C₂H₅ | H | H | O |
| 321 | H | CON(CH₃)C₂H₅ | H | H | S |
| 322 | H | CONHCH₂C₆H₅ | H | H | S |
| 323 | H | CONHCH₂CH₂CH=CF₂ | H | H | O |
| 324 | H | CONHCH₂CH₂CH=CF₂ | H | H | S |
| 325 | H | CONHCH₂CH₂CH₃ | H | H | O |
| 326 | H | CONHCH₃ | H | H | O |
| 327 | H | CONHSO₂CH₃ | H | H | O |
| 328 | H | CONHSO₂CH₃ | H | H | S |
| 329 | H | COSCH₂CH₂CH=CF₂ | H | H | O |
| 330 | H | COSCH₂CH₂CH=CF₂ | H | H | S |
| 331 | H | CSNH₂ | H | H | O |
| 332 | H | F | H | H | O |
| 333 | H | F | H | H | O |
| 334 | H | F | F | H | S |
| 335 | H | I | H | H | O |
| 336 | H | N(SO₂CH₃)₂ | H | H | O |
| 337 | H | N(SO₂CH₃)₂ | H | H | S |
| 338 | H | NH₂ | H | H | S |
| 339 | H | NHCHO | H | H | O |
| 340 | H | NHCHO | H | H | S |

TABLE I-continued

| COMPOUND NO. | R¹ | R² | R³ | R⁴ | X |
|---|---|---|---|---|---|
| 341 | H | NHCOC$_2$H$_5$ | H | H | O |
| 342 | H | NHCOC$_2$H$_5$ | H | H | S |
| 343 | H | NHCOC$_6$H$_5$ | H | H | O |
| 344 | H | NHCOCH$_3$ | H | H | O |
| 345 | H | NHCOCH$_3$ | H | H | S |
| 346 | H | NHSO$_2$CH$_3$ | H | H | O |
| 347 | H | NHSO$_2$CH$_3$ | H | H | S |
| 348 | H | NO$_2$ | H | H | O |
| 349 | H | NO$_2$ | NO$_2$ | H | S |
| 350 | H | OCF$_2$CF$_2$H | H | H | O |
| 351 | H | OCF$_2$CF$_2$H | H | H | S |
| 352 | H | OCF$_2$H | H | H | O |
| 353 | H | OCF$_2$H | H | H | O |
| 354 | H | OCF$_2$H | H | H | O |
| 355 | H | OCF$_2$H | H | H | S |
| 356 | H | OCF$_2$H | H | H | S |
| 357 | H | OCF$_2$H | H | H | S |
| 358 | H | OCF$_3$ | H | H | O |
| 359 | H | OCH(CH$_3$)C$_2$H$_5$ | H | H | O |
| 360 | H | OCH(CH$_3$)C$_2$H$_5$ | H | H | S |
| 361 | H | OCH$_2$CCl=CH$_2$ | H | H | O |
| 362 | H | OCH$_2$CCl=CH$_2$ | H | H | S |
| 363 | H | OCH$_2$CF$_3$ | H | H | O |
| 364 | H | OCH$_2$CF$_3$ | H | H | S |
| 365 | H | OCH$_2$CH=CCl$_2$ | H | H | O |
| 366 | H | OCH$_2$CH=CCl$_2$ | H | H | S |
| 367 | H | OCH$_2$CH=CH$_2$ | H | H | O |
| 368 | H | OCH$_2$CH=CH$_2$ | H | H | S |
| 369 | H | OCH$_2$CH$_2$CH=CF$_2$ | H | H | O |
| 370 | H | OCH$_2$CH$_2$CH=CF$_2$ | H | H | S |
| 371 | H | OCH$_2$CH$_2$CH$_3$ | H | H | O |
| 372 | H | OCH$_2$CH$_2$CH$_3$ | H | H | S |
| 373 | H | OCH$_2$CH$_2$F | H | H | O |
| 374 | H | OCH$_2$CH$_2$F | H | H | S |
| 375 | H | OCH$_2$CH$_3$ | H | H | O |
| 376 | H | OCH$_2$CH$_3$ | H | H | O |
| 377 | H | OCH$_2$CH$_3$ | H | H | S |
| 378 | H | OCH$_2$CH$_3$ | H | H | S |
| 379 | H | OCH$_2$CO$_2$C$_2$H$_5$ | H | H | O |
| 380 | H | OCH$_2$CO$_2$C$_2$H$_5$ | H | H | S |
| 381 | H | OCH$_3$ | H | H | O |
| 382 | H | OCH$_3$ | H | H | O |
| 383 | H | OCH$_3$ | H | H | S |
| 384 | H | OCH$_3$ | H | H | S |
| 385 | H | OCOCH$_3$ | H | H | O |
| 386 | H | OCOCH$_3$ | H | H | S |
| 387 | H | OH | H | H | S |
| 388 | H | OSO$_2$CH$_3$ | H | H | O |
| 389 | H | OSO$_2$CH$_3$ | H | H | S |
| 390 | H | SCF$_3$ | H | H | O |
| 391 | H | SCF$_3$ | H | H | O |
| 392 | H | SCF$_3$ | H | H | O |
| 393 | H | SCH$_2$CH$_2$CH$_3$ | H | H | O |
| 394 | H | SO$_2$CF$_3$ | H | H | O |
| 395 | H | SO$_2$CH$_3$ | H | H | O |
| 396 | H | SO$_2$F | H | H | O |
| 397 | H | SO$_2$F | H | H | S |
| 398 | H | SO$_2$N(C$_2$H$_5$)$_2$ | H | H | S |
| 399 | H | SO$_2$N(CH$_3$)$_2$ | H | H | O |
| 400 | H | SO$_2$NH$_2$ | H | H | O |
| 401 | H | SO$_2$NH$_2$ | H | H | S |
| 402 | H | SO$_2$NHCH$_3$ | H | H | O |
| 403 | H | SOCF$_3$ | H | H | O |
| 404 | H | SOCH$_3$ | H | H | O |
| 405 | H | H | H | Cl | O |
| 406 | H | H | H | CO$_2$CH$_3$ | S |
| 407 | H | H | H | CONHCH$_2$C$_6$H$_5$ | S |
| 408 | H | H | H | COOH | S |
| 409 | H | H | H | NH$_2$ | S |
| 410 | H | H | H | NHCOC$_2$H$_5$ | S |
| 411 | H | H | H | NHCOCF$_3$ | S |
| 412 | H | H | H | NHSO$_2$CH$_3$ | S |
| 413 | H | H | H | NO$_2$ | S |
| 414 | H | H | H | OCH$_2$CH$_2$CH=CF$_2$ | S |
| 415 | H | H | H | OCH$_2$CH$_2$F | S |
| 416 | H | H | H | OCOC$_2$H$_5$ | S |
| 417 | H | H | H | OH | S |
| 418 | H | H | Br | H | O |
| 419 | H | H | CH$_2$OCH$_3$ | H | O |
| 420 | H | H | COOH | H | O |

TABLE I-continued

| COMPOUND NO. | R$^1$ | R$^2$ | R$^3$ | R$^4$ | X |
|---|---|---|---|---|---|
| 421 | H | H | OCH$_3$ | H | O |
| 422 | H | H | OH | H | O |
| 423 | H | H | CN | H | O |
| 424 | H | H | OCH$_3$ | H | O |
| 425 | H | H | F | H | O |
| 426 | H | H | OCH$_3$ | H | O |
| 427 | H | H | cc H | H | S |
| 428 | H | H | CH$_2$CH=CH$_2$ | H | S |
| 429 | H | H | CH$_3$ | H | S |
| 430 | H | H | CO$_2$CH$_3$ | H | S |
| 431 | H | H | COOH | H | S |
| 432 | H | H | F | H | S |
| 433 | H | H | OCH | H | S |
| 434 | H | H | OH | H | S |
| 435 | H | H | CN | H | S |
| 436 | H | H | OCH$_3$ | H | S |
| 437 | H | H | H | H | S |
| 438 | H | H | OCH$_3$ | H | S |
| 439 | CH=CH | H | H | H | S |
| 440 | CH=CH$_2$ | H | H | H | O |
| 441 | H | CH=CH$_2$ | H | H | O |
| 442 | H | CH=CH$_2$ | H | H | S |

$^c$indicates a cyclic substituent.

The process of step (a) of the invention described above has not previously been reported. Accordingly, in another aspect, the invention provides a process of making an optionally substituted 2-mercaptobenz-oxazole or -thiazole having the formula (III) wherein R$^1$-R$^4$ are as hereinbefore defined, which comprises reacting an optionally substituted ortho-nitro or -nitroso phenol or ortho-nitro or -nitroso thiophenol of formula (II) wherein R$^1$-R$^4$ are as hereinbefore defined, y is 1 or 2, and X is oxygen or sulphur, with a reducing agent comprising an alkali metal dithionite in an alkaline reaction medium in the presence of carbon disulphide to form the optionally substituted 2-mercaptobenz-oxazole or -thiazole of formula (III), acidifying the reaction medium, and collecting the 2-mercaptobenz-oxazole or -thiazole.

Compounds of formula (IV) wherein L is OSO$_2$R$^a$ may be prepared by the following sequence of reactions. Hydrogen bromide is reacted with the commercially available compound of Formula (V) under standard conditions for an addition reaction, for example by passing hydrogen bromide gas through a solution of the compound of Formula (V) in an inert solvent, optionally in the presence of a free-radical generator (e.g. benzoyl peroxide) to give the compound of formula (VI). The compound of formula (VI) is then reacted with the silver salt of a sulphonic acid of formula R$^a$-SO$_3$H, wherein R$^a$ has the meaning given above, for example the silver salt of 4-methylbenzenesulphonic acid (silver tosylate) or the silver salt of methanesulphonic acid (silver mesylate), preferably in an inert solvent in the absence of light, to give the corresponding compound of Formula (VII). Debromofluorination of the compound of formula (VII), for example by reaction with zinc, preferably in the presence of a suitable catalyst such as iodine, gives the compound (III), wherein R$^a$ has the meanings given above.

The compound of formula (IV) wherein L is bromine, i.e. 4-bromo-1,1-difluorobut-1-ene may be prepared by the following sequence of reactions: Hydrogen bromide is reacted with the commercially available compound 4-bromo-1,1,2-trifluorobut-1-ene having the formula (V), under standard conditions for an addition reaction, for example by passing hydrogen bromide gas through a solution of 4-bromo-1,1,2-trifluorobut-1-ene in an inert solvent, optionally in the presence of a free radical generator (e.g. benzoyl peroxide), to give 1,4-dibromo-1,1,2-trifluorobutane (Formula (VI). This compound is then treated with a debromofluorinating agent, which removes a bromine atom and a fluorine atom from the 1,4-dibromo-1,1,2-trifluorobutane to give 4-bromo-1,1-difluorobut-1-ene (IV, L=Br). Examples of debromofluorinating agents include zinc, magnesium and aluminium.

Compounds of formula (IV) wherein L is another halogen atom may be prepared in a similar way to that described above wherein L is bromine.

Various preferred features and embodiments of the present invention will now be described by way of non-limiting example with reference to the following Examples.

Examples 1 to 4 illustrate step (a) of the process of the present invention.

EXAMPLE 1

Preparation of 6-methoxy-2-mercaptobenzoxazole

Carbon disulphide (9 ml, 0.15 mol) was added dropwise over a period of 1 minute to a solution of potassium hydroxide (6.5 g, 0.12 mol) in a mixture of water (10 ml) and methanol (100 ml), followed by 2-nitro-5-methoxyphenol (16.9 g, 0.1 mol). ]The 2-nitro-5-methoxyphenol required as starting material was prepared by nitration of 3-methoxyphenol as described in Synthetic Communications, 1993, 23(3) 343–348.] To this mixture was added dropwise a solution of potassium hydroxide (39 g, 0.7 mol) and sodium dithionite (65 g, 0.3 mol), over a period of 15 minutes, so that the temperature did not exceed 40° C. The reaction mixture was then cooled to room temperature and carbon disulphide (0.9 ml, 0.15 mol) added and the resulting solution heated to 80° C. for 2 hours. The mixture was then cooled and acidified with concentrated hydrochloric acid to a pH of 3. The pale yellow precipitate was collected and air dried to yield 6-methoxy-2-mercaptobenzoxazole (16.6 g, 89%).

Proton NMR (CDCl$_3$): δ 2.85(3H, OCH$_3$); 6.9(1H, dd, aromatic C—H); 6.95(1H, d, aromatic C—H); 7.13(H, d, aromatic C—H); 11.0 (H, bs, SH).

Following the above procedure, 6-methoxy-2-mercaptobenzthiazole may be prepared in a similar way, using 2-nitro thiophenol as starting material.

EXAMPLE 2

Preparation of 6-hydroxy-2-mercaptobenzoxazole

Carbon disulphide (0.9 ml, 15 mmol) was added to a solution of potassium hydroxide (0.65 g, 11 mmol) in a mixture of water (1 ml) and methanol (10 ml), followed by 4-nitro 1,2-benzenediol (1.5 g, 10 mmol). To this mixture was added dropwise a solution of sodium dithionite (6,5 g, 30 mmol) and potassium hydroxide (3.9 g, 70 mmol) in water (50 ml); strong heat evolution was observed. After 10 minutes, carbon disulphide (0.9 ml, 15 mmol) was added and the mixture heated to 75° C. for 3 hours. The mixture was then cooled in an ice bath and the precipitate filtered off. The filtrate was acidified to approximately pH3 with concentrated hydrochloric acid and the yellow precipitate was collected, washed with water and air dried. The yield was 1.05 g (65%).

Proton NMR (CDCl$_3$): δ 3.30(1H, bs, OH); 7.68(1H, dd, aromatic C—H); 6.84(1H, d, aromatic C—H); 7.00(1H, d, aromatic C—H) and 9.75 (1H, bs, SH).

EXAMPLE 3

Preparation of 5-methoxy-2-mercaptobenzoxazole

Carbon disulphide (886 mg, 0.7 ml, 11.6 mmol) was added dropwise to KOH (800 mg, 14.3 mmol) dissolved in methanol (8 ml) and water (15 ml), and the resulting yellow solution stirred for 4 minutes at room temperature. This was added to a mixture of 3-methoxy-6-nitrophenol (1.2 g, 7.1 mmol), KOH (2.0 g, 35.7 mmol) and water (35 ml), followed by the addition of first solid sodium dithionite (3.7 g, 21.2 mmols), then carbon disulphide (760 mg, 9.9 mmol). The resulting mixture was stirred at 70° C. for 20 hours.

The reaction mixture was cooled to room temperature, acidified with concentrated HCl and the resulting precipitated solid collected by filtration and air dried. The yield was 980 mg (76%).

Proton NMR (CDCl$_3$/D$_6$-DMSO): δ 3.80 (3H, s, OCH$_3$), 6.75 (2H, m, aromatic C—H), 7.50 (1H, d, aromatic C—H), and 13.20 (1H, bs, SH).

EXAMPLE 4

Preparation of 5-trifluoromethyl-2-mercaptobenzthiazole

Carbon disulphide (2.28 g, 30 mmol) was added dropwise over a period of 1 minute to a solution of potassium hydroxide (0.33 g, 5.9 mmol) in a mixture of water (2 ml) and methanol (5 ml), and the resulting yellow solution stirred for 5 minutes, followed by the addition of 2-nitro-4-trifluoromethyl thiophenol (1.10 g, 5 mmol). To this mixture was added dropwise over a period of 5 minutes a solution of potassium hydroxide (1.97 g, 35 mmol) and sodium dithionite (3.1 g, 15 mmol) in water (14 ml), so that the temperature did not exceed 40° C. The resultant orange mixture was stirred at 40°–50° C. for 2 hours. The reaction mixture was cooled to 10° C. and slowly acidified to pH 5–6 with concentrated HCl, and the mixture stirred for half an hour at this temperature. The off-white solid was washed with water and air dried to give the product. The yield was 0.81 g (70%).

Proton NMR (CDCl$_3$): δ 7.45 (1H, d, aromatic C—H), 7.50 (1H, d, aromatic C—H), 7.55 (1H, s, aromatic C—H) and 13.50 (1H, bs, SH);

mass spectrum (EI/CI) 251 (M$^+$+NH$^+_4$), 236 (MH$^+$).

Examples 5 and 6 illustrate step (b) of the process of the present invention.

EXAMPLE 5

Preparation of 2-(4,4-difluorobut-3-enyl) thiobenzoxazole (Compound No. 2)

2-Mercaptobenzoxazole (4.79 g) was added to a solution of 1,1-difluorobut-1-en-4-yl 4-methylbenzenesulphonate (6.4 g) in acetone (200 cm$^3$) containing potassium carbonate (5.06 g). The mixture was heated to reflux overnight (17 hr) and gc used to confirm that the 1,1-difluorobut-1-en-4-yl 4-methylbenzenesulphonate had been consumed and the product had formed. The reaction mass was allowed to cool and was filtered through a plug of High-Flo filter aid to remove insoluble inorganic material. The solid material was washed with ethyl acetate and the combined organic portions evaporated under reduced pressure to give 7.1 g of a brown oily residue. This material was fractionated by eluting through a bed of silica using hexane/ethyl acetate (40:1 by volume) as solvent to give the required product as a colourless oil (5.4 g, 92% based on the sulphonate); M$^+$=241;

Proton NMR (CDCl$_3$): δ 2.5–2.6 (m, 2H), 3.3–3.4 (t, 2H), 4.2–4.4 (m, 1H), 7.2–7.35 (m, 2H), 7.45 (dd, 1H), 7.6 (dd, 1H).

EXAMPLE 6

Preparation of 2-(4,4-difluorobut-3-enyl) thio-4-nitrobenzoxazole (Compound No. 81)

To a brown stirred suspension of 2-mercapto-4-nitrobenzoxazole (Example 2C, 550 mg) and potassium carbonate (375 mg) in acetone (15 cm$^3$) was added 4,4-difluorobut-3-enyl p-tolylsulphonate (700 mg) and the mixture was heated under reflux for 21 hours. The reaction was quenched by the addition of water, and extracted three times with ethyl acetate. The combined organic layers were washed with water, brine and dried (MgSO$_4$). Filtration and evaporation under reduced pressure gave a brown solid (806 mg). Recrystallisation from ethyl acetate and hexane gave 2-[4,4-difluorobut-3-enylthio]-4-nitrobenzoxazole as a brown crystalline solid (396 mg). GC analysis indicated that the material was >99% pure.

Proton NMR (CDCl$_3$) δ: 8.14(1H,d); 7.75(1H,d); 7.39(1H,t); 4.34(1H,m); 3.48(2H,t); 2.61(2H,m).

It will be appreciated that Examples 5 and 6 illustrate a general procedure for the preparation of 2-(4,4-difluorobut-3-enyl) thio-substituted benzoxazoles and benzthiazoles, and that the intermediates prepared in Examples 1 to 4 can be reacted in an analogous fashion to prepare the corresponding final product. Similarly the benzoxazole compounds used in Examples 5 and 6 can be prepared in accordance with the procedure illustrated in Examples 1 to 4.

CHEMICAL FORMULAE
(IN DESCRIPTION)

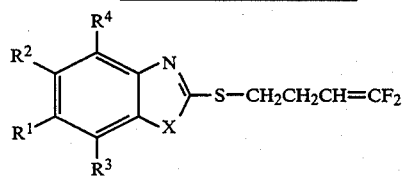

(I)

-continued
CHEMICAL FORMULAE
(IN DESCRIPTION)

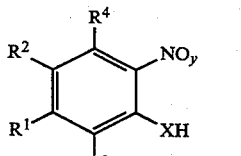

(II)

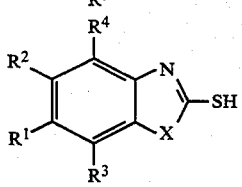

(III)

CF$_2$=CH—CH$_2$—CH$_2$—L   (IV)
CF$_2$=C(F)—CH$_2$—CH$_2$—Br   (V)

CF$_2$BrCHFCH$_2$CH$_2$Br   (VI)
CF$_2$BrCHFCH$_2$CH$_2$OSO$_2$R$^a$   (VII)

We claim:
1. A process for the preparation of a compound of formula (I)

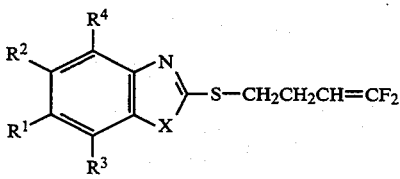

(I)

wherein R$^1$, R$^2$, R$^3$, and R$^4$ are each independently hydrogen, optionally substituted alkyl, optionally substituted alkenyl, alkynyl, cycloalkyl, alkylcycloalkyl, optionally substituted aryl, optionally substituted arylalkyl, optionally substituted aryloxy, optionally substituted arylalkoxy, alkoxy, alkenyloxy, alkynyloxy, hydroxyalkyl, alkoxyalkyl, alkylthio, alkenylthio, alkynylthio, haloalkyl, haloalkenyl, haloalkynyl, haloalkoxy, haloalkenyloxy, haloalkynyloxy, haloalkylthio, haloalkenylthio, haloalkynylthio, halogen, hydroxy, cyano, nitro, —NR$^5$R$^6$, —NR$^7$COR$^8$, —NR$^7$CSR$^8$, —NR$^9$SO$_2$R$^{10}$, —N(SO$_2$—R$^{11}$), —(SO$_2$—R$^{12}$), —COR$^{13}$, —CONR$^{14}$R$^{15}$, —COOR$^{16}$, —OCOR$^{17}$, —OSO$_2$R$^{18}$, —SO$_2$NR$^{19}$R$^{20}$, —SO$_2$R$^{21}$, —SOR$^{22}$, —CSNR$^{23}$R$^{24}$, —SiR$^{25}$R$^{26}$R$^{27}$, —OCH$_2$CO$_2$R$^{28}$, —OCH$_2$CH$_2$CO$_2$R$^{29}$, —SO$_2$Z, —CONR$^{30}$SO$_2$R$^{31}$, —NHCONR$^{32}$R$^{33}$, —NHCSNR$^{32}$R$^{33}$ or an adjacent pair of R$^1$, R$^2$, R$^3$ and R$^4$ when taken together form a fused 5- or 6-membered carbocyclic or heterocyclic ring; R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$, R$^{32}$ and R$^{33}$ are each independently selected from hydrogen, alkyl, alkenyl, alkynyl, haloalkyl, haloalkenyl, haloalkynyl, optionally substituted aryl and optionally substituted arylalkyl; Z is halogen; and X is oxygen or sulphur, which comprises (a) reacting a substituted ortho-nitro or -nitroso phenol or a substituted ortho-nitro or -nitroso thiophenol of formula (II),

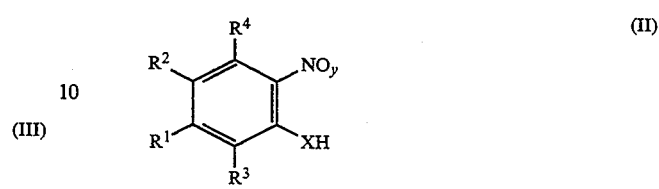

(II)

wherein R$^1$–R$^4$ and X have the values previously defined, and y is 1 or 2, with a reducing agent comprising an alkali metal dithionite in an alkaline reaction medium in the presence of carbon disulphide, to form the substituted 2-mercaptobenz-oxazole or -thiazole of formula (III)

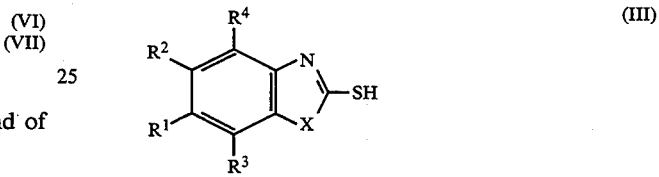

(III)

wherein R$^1$–R$^4$ and X have the values previously defined, acidifying the reaction mixture and collecting the 2-mercaptobenz-oxazole or -thiazole; and (b) reacting the 2-mercaptobenz-oxazole or -thiazole (III), with a compound of formula (IV)

CF$_2$=CH—CH$_2$—CH$_2$—L   (IV)

wherein L is a good leaving group to form the compound of formula (I).

2. A process according to claim 1, in which L is a halogen atom, or an OSO$_2$R$^a$ group wherein R$^a$ is a C$_{1-4}$ alkyl group, or a phenyl group optionally substituted with a C$_{1-4}$ alkyl group.

3. A process according to claim 1, in which the reaction of the compound of formula (III) with a compound of formula (IV) is carried out at a temperature in the range of about 40°–100° C.

4. A process according to claim 1, in which the alkali metal dithionite reducing agent is sodium dithionite.

5. A process according to claim 1, in which the alkaline reaction medium is an aqueous alcoholic solution of an alkali metal hydroxide.

6. A process according to claim 1, in which the alkaline reaction medium is a solution of sodium or potassium hydroxide in methanol or ethanol containing water.

7. A process according to claim 1, in which a compound of formula (II) is reacted to form a compound of formula (III) at a temperature of from room temperature to about 80° C.

* * * * *